US012688908B2

(12) United States Patent
Wilson

(10) Patent No.: US 12,688,908 B2
(45) Date of Patent: Jul. 21, 2026

(54) SYSTEMS AND METHODS USING DNA SEQUENCE STRINGS AS A COMMON DATA FORMAT FOR FORENSIC DNA TYPING APPLICATIONS

(71) Applicant: BATTELLE MEMORIAL INSTITUTE, Columbus, OH (US)

(72) Inventor: Mark R. Wilson, Fredericksburg, VA (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 4 days.

(21) Appl. No.: 18/947,474

(22) Filed: Nov. 14, 2024

(65) Prior Publication Data

US 2025/0069698 A1 Feb. 27, 2025

Related U.S. Application Data

(63) Continuation of application No. 18/135,603, filed on Apr. 17, 2023, now Pat. No. 12,183,435, which is a
(Continued)

(51) Int. Cl.
*G06F 16/00* (2019.01)
*G06F 16/13* (2019.01)
(Continued)

(52) U.S. Cl.
CPC ............. *G16B 30/00* (2019.02); *G06F 16/13* (2019.01); *G06F 16/148* (2019.01); *G16B 50/00* (2019.02)

(58) Field of Classification Search
None
See application file for complete search history.

(56) References Cited

U.S. PATENT DOCUMENTS 11,664,088 B2 5/2023 Wilson
2003/0211486 A1 11/2003 Frudakis
(Continued)

FOREIGN PATENT DOCUMENTS

EP 2513341 B1 * 4/2017 ........... C12Q 1/6827
JP 2004537292 A 12/2004
(Continued)

OTHER PUBLICATIONS

European Patent Office, PCT Search Report and Written Opinion prepared for PCT/US2017/044563, completed Oct. 12, 2017, 13 pages.
(Continued)

*Primary Examiner* — Tuankhanh D Phan
(74) *Attorney, Agent, or Firm* — Barnes & Thornburg LLP

(57) ABSTRACT

The present disclosure relates, generally, to nucleotide sequence data and, more particularly, to computer files and methods supporting forensic DNA analysis. In one illustrative embodiment, a method may comprise identifying a locus corresponding to each item of short tandem repeat (STR) profiling data stored in an existing computer file, wherein the STR profiling data stored in the existing computer file is repeat-based and/or length-based; identifying start and stop coordinates of an STR region of the corresponding locus for each item of STR profiling data stored in the existing computer file; creating an ambiguous text string corresponding to each item of STR profiling data stored in the existing computer file, wherein each ambiguous text string consists of a sequence of ambiguous characters extending from the start coordinate to the stop coordinate identified for the corresponding item of STR profiling data; and storing each ambiguous text string in a sequence-based computer file.

16 Claims, 3 Drawing Sheets

Specification includes a Sequence Listing.

Related U.S. Application Data continuation of application No. 16/321,681, filed as application No. PCT/US2017/044563 on Jul. 30, 2017, now Pat. No. 11,664,088.

(60) Provisional application No. 62/369,066, filed on Jul. 30, 2016.

(51) Int. Cl.
  G06F 16/14      (2019.01)
  G16B 30/00      (2019.01)
  G16B 50/00      (2019.01)

(56)              References Cited

U.S. PATENT DOCUMENTS

| | | | | |
|---|---|---|---|---|
| 2014/0114582 A1* | 4/2014 | Mittelman | ............. | G16B 20/20 |
| | | | | 702/19 |
| 2014/0278127 A1 | 9/2014 | Young et al. | | |
| 2016/0010146 A1 | 1/2016 | Green | | |
| 2023/0377687 A1 | 11/2023 | Wilson | | |

FOREIGN PATENT DOCUMENTS

| | | | | |
|---|---|---|---|---|
| WO | WO-2004055646 A2 * | 7/2004 | ............. | G16B 45/00 |
| WO | 2014015346 A1 | 1/2014 | | |

OTHER PUBLICATIONS

Denoeud et al., "Predicting Human Minisatellite Polymorphism," Genome Research, Apr. 2003, pp. 856-867, vol. 13, Cold Spring Harbor Laboratory Press.

* cited by examiner

Example: 162 bp = 7 repeats, allele '7' by size

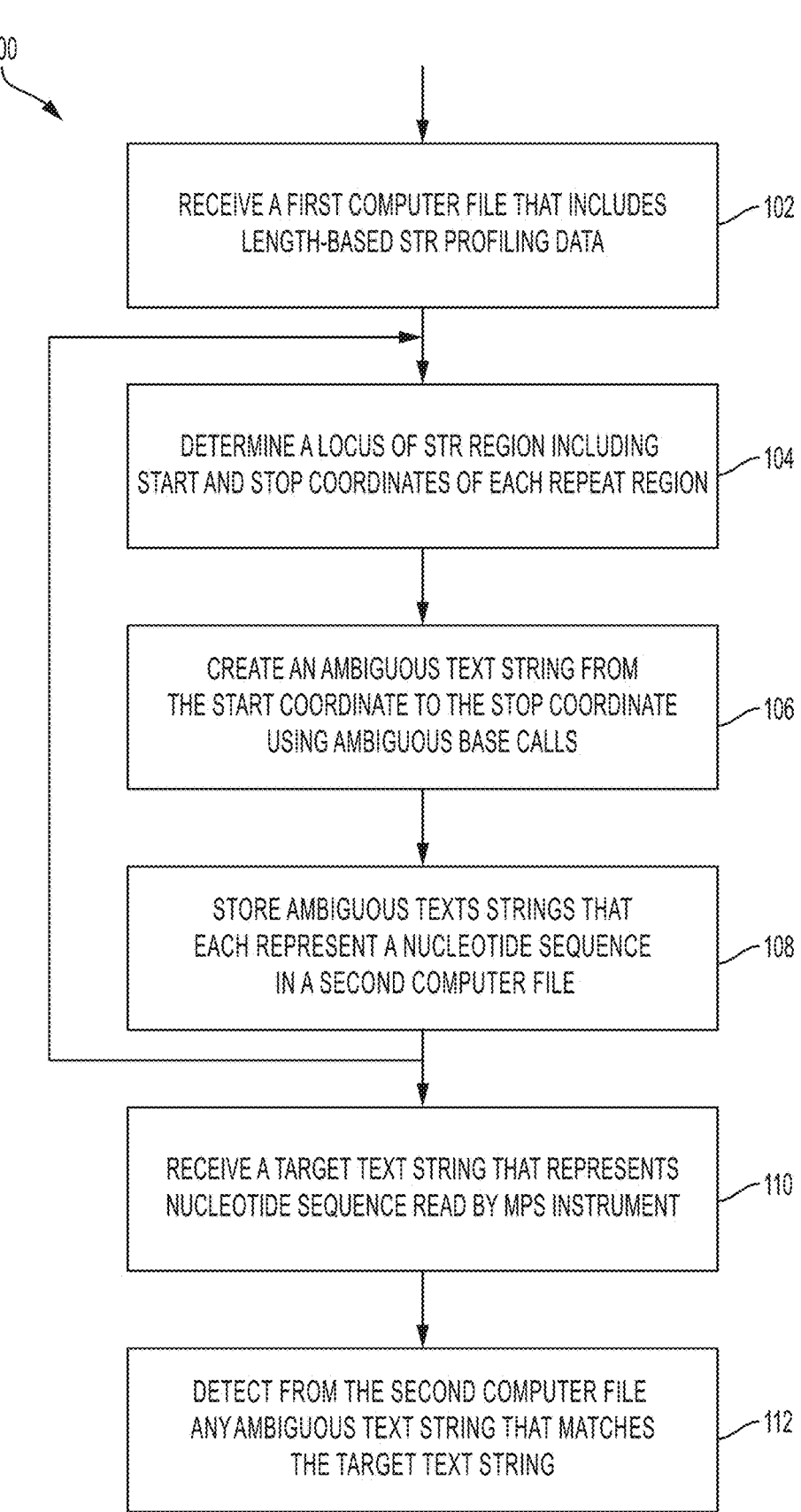

100

RECEIVE A FIRST COMPUTER FILE THAT INCLUDES
LENGTH-BASED STR PROFILING DATA — 102

DETERMINE A LOCUS OF STR REGION INCLUDING
START AND STOP COORDINATES OF EACH REPEAT REGION — 104

CREATE AN AMBIGUOUS TEXT STRING FROM
THE START COORDINATE TO THE STOP COORDINATE
USING AMBIGUOUS BASE CALLS — 106

STORE AMBIGUOUS TEXTS STRINGS THAT
EACH REPRESENT A NUCLEOTIDE SEQUENCE
IN A SECOND COMPUTER FILE — 108

RECEIVE A TARGET TEXT STRING THAT REPRESENTS
NUCLEOTIDE SEQUENCE READ BY MPS INSTRUMENT — 110

DETECT FROM THE SECOND COMPUTER FILE
ANY AMBIGUOUS TEXT STRING THAT MATCHES
THE TARGET TEXT STRING — 112

FIG. 5

SEQUENCE LISTING

```
Sequence total quantity: 1
SEQ ID NO: 1            moltype = DNA  length = 31
FEATURE                 Location/Qualifiers
misc_feature            1..31
                        note = Description of Artificial Sequence: Synthetic
                         oligonucleotide
source                  1..31
                        mol_type = other DNA
                        organism = synthetic construct
SEQUENCE: 1
gttagctagg cttgtaggct ctctgtatta t                                      31
```

SYSTEMS AND METHODS USING DNA SEQUENCE STRINGS AS A COMMON DATA FORMAT FOR FORENSIC DNA TYPING APPLICATIONS

CROSS-REFERENCE TO RELATED APPLICATIONS

This application is a continuation of U.S. patent application Ser. No. 18/135,603, filed Apr. 17, 2023, which is a continuation of U.S. patent application Ser. No. 16/321,681, filed Jan. 29, 2019, now U.S. Pat. No. 11,664,088, which is a national stage entry of PCT International Application No. PCT/US2017/044563, filed Jul. 30, 2017, and claims priority to U.S. Provisional Application Ser. No. 62/369,066, filed on Jul. 30, 2016. The entire disclosure of each of the foregoing applications is incorporated herein by reference.

SEQUENCE LISTING

The instant application contains a Sequence Listing which has been filed electronically in XML format and is hereby incorporated herein by reference in its entirety. Said XML copy, created on Nov. 14, 2024, is named 17760USCON1_416349_SL.xml and is 2,480 bytes in size.

TECHNICAL FIELD

The present disclosure relates, generally, to nucleotide sequence data and, more particularly, to computer files and methods supporting forensic DNA analysis.

BACKGROUND ART

Polymorphic tandem repeats of nucleotide sequences are found throughout genomes, and the particular combinations of allelic states at multiple repeat sites are sufficiently unique to an individual that these repeating sequences can be used in human or other organism identification. These markers are also useful in genetic mapping and linkage analysis, where the tandem repeat sites may be linked to sites important for determining, for example, predisposition for disease. Tandem repeats can be used directly in human identity testing, such as in forensic analysis of DNA. There are many types of tandem repeats in genome sequences. Those used in forensic DNA typing fall under the general term variable number tandem repeats (VNTR).

One application of VNTR analysis is in forensics or human identity testing. In current forensics analyses, highly polymorphic short tandem repeats (STRs) are identified using a DNA sample from an individual and DNA amplification steps, such as polymerase chain reaction (PCR), to provide enriched DNA sequences, or amplicons, from the individual's starting genomic DNA. The amplicons can then be matched by size to reference samples, such as the sequences stored in national or local DNA databases or samples obtained in a case. For example, amplicons that originate from STR loci can be matched to reference STR databases, including the FBI CODIS database in the United States, or the NDNAD database in Europe, to identify the individual by matching to the STR alleles (i.e., different forms of DNA by sequence, or size and sequence, found at a particular locus) found in evidentiary or reference samples.

With the advent of next-generation DNA sequencing, also called Massively Parallel DNA sequencing (MPS), DNA sequencing of repeat-based markers such as STRs, is now practical. However, conversion of the old repeat-based typ-ing naming system to the new DNA sequence-based system is needed. It is practicable to continue to use the existing repeat-based markers for back-compatibility to voluminous DNA databases, but the names given to each allele in the repeat-based system do not describe the complexity present in the full DNA sequence. The inventor of the present disclosure has determined that, with an appropriate inter-conversion between repeat-based data and DNA sequence-based data, the old repeat-based typing nomenclature could be subsumed into the new, sequence-based typing method, resulting in no loss of information and a promise of much wider efficacy and comparability across different technolo-gies.

Current STR nomenclature designates the number of repeats as the allelic type for a locus. The number of repeats may be inferred from the entire size of the amplified DNA fragment as compared to a standard number of repeats that correlates a particular size to a particular repeat number. This naming scheme is appropriate for repeat-based differ-ences, but inappropriate for describing sequence-based dif-ferences. Rather, the entire DNA sequence, extending primer-to-primer in the case of amplified targets, should be considered as the allele, rather than the number of repeats or even the sequence obtained within the repeated region. This approach obviates the necessity to identify the boundaries of the repeat region, which can be ambiguous and confusing.

Because of the wealth of data collected using repeat-based designations, however, back-compatibility issues arise when one attempts to convert a DNA sequence string to the number of repeats, and vice-versa. STR typing by amplicon fragment size, using an instrument that measures the size of the fragment, does not contain any sequence information, and hence a conversion system is needed that allows back-compatibility with existing and voluminous databases of alleles typed by size and stored as a corresponding number of repeats found at each locus.

SUMMARY OF INVENTION

Illustrative embodiments of the invention are described in the following enumerated clauses. Any combination of the following clauses is contemplated, along with any appli-cable combination with the embodiments described in the Detailed Description of Illustrative Embodiments below.

1. A method comprising creating an ambiguous text string corresponding to each item of short tandem repeat (STR) profiling data stored in an existing computer file, wherein each ambiguous text string consists of a sequence of ambiguous characters extending from a start coordinate to a stop coordinate identified for the corresponding item of STR profiling data.

2. The method of clause 1, wherein the STR profiling data stored in the existing computer file is repeat-based and/or length-based.

3. The method of clause 1 or clause 2, further comprising identifying a locus corresponding to each item of STR profiling data stored in the existing computer file.

4. The method of any one of clauses 1-3, wherein the start and stop coordinates identified for each item of STR pro-filing data are the start and stop coordinates of an STR region of the corresponding locus for that item of STR profiling data.

5. The method of any one of clauses 1-4, further com-prising storing each ambiguous text string in a sequence-based computer file.

6. The method of any one of clauses 1-5, wherein each ambiguous character of each ambiguous text is a text character used to represent an ambiguous base call.

7. The method of clauses 1-6, further comprising storing, in the sequence-based computer file, data representing the locus identified for each item of STR profiling data together with the ambiguous text string created for each item of STR profiling data.

8. The method of any one of clauses 1-7, further comprising storing, in the sequence-based computer file, data representing the start and stop coordinates identified for each item of STR profiling data together with the ambiguous text string created for each item of STR profiling data.

9. The method of any one of clauses 1-8, wherein identifying start and stop coordinates of the STR region of the corresponding locus for each item of STR profiling data stored in the existing computer file comprises, for each item of STR profiling data, mapping primers used for polymerase chain reaction (PCR) amplification of the STR region of the corresponding locus to a reference standard.

10. The method of clause 9, wherein the reference standard is a human genome build.

11. The method of clause 9, wherein the start and stop coordinates are identified such that the primers do not contribute to the length of the ambiguous text string created for each item of STR profiling data stored in the existing computer file.

12. The method of any one of clauses 1-11, wherein the existing computer file represents a DNA profile of a human.

13. The method of any one of clauses 1-12, wherein the existing computer file has been retrieved from a Combined DNA Index System (CODIS) database.

14. The method of any one of clauses 1-12, wherein the existing computer file has been retrieved from the United Kingdom National DNA Database (NDNAD).

15. The method of any one of clauses 1-14, wherein the existing computer file comprises a plurality of items of short tandem repeat (STR) profiling data.

16. The method of any one of clauses 1-15, further comprising repeating the steps of the method for a plurality of existing computer files storing repeat-based and/or length-based STR profiling data.

17. The method of clause 16, wherein repeating the steps of the method results in a plurality of sequence-based computer files storing ambiguous text strings.

18. The method of clause 17, further comprising storing the plurality of sequence-based computer files in a database.

19. The method of any one of clauses 1-15, further comprising receiving a target text string that represents nucleotide sequence data generated by a read of a massively parallel sequencing (MPS) instrument and comparing the target text string to each ambiguous text string in the sequence-based computer file to detect any ambiguous text string in the sequence-based computer file that matches the target text string.

20. The method of clause 17 or clause 18, further comprising receiving a target text string that represents nucleotide sequence data generated by a read of a massively parallel sequencing (MPS) instrument and comparing the target text string to each ambiguous text string in the plurality of sequence-based computer files to detect any ambiguous text string in the plurality of sequence-based computer files that matches the target text string.

21. The method of any one of clauses 1-15, further comprising receiving a target computer file comprising a plurality of target text strings, wherein each target text string represents nucleotide sequence data generated by a read of a massively parallel sequencing (MPS) instrument, and comparing each of the plurality of target text strings to each ambiguous text string in the sequence-based computer file to detect any ambiguous text string in the sequence-based computer file that matches any of the target text strings.

22 The method of clause 17 or clause 18, further comprising receiving a target computer file comprising a plurality of target text strings, wherein each target text string represents nucleotide sequence data generated by a read of a massively parallel sequencing (MPS) instrument, and comparing each of the plurality of target text strings to each ambiguous text string in the plurality of sequence-based computer files to detect any ambiguous text string in the plurality of sequence-based computer files that matches any of the target text strings.

23. The method of clause 15, further comprising receiving a target computer file comprising a plurality of target text strings, wherein each target text string represents nucleotide sequence data generated by a read of a massively parallel sequencing (MPS) instrument, and comparing the plurality of target text strings to the ambiguous text strings in the sequence-based computer file to detect whether each of the target text strings matches at least one of the ambiguous text strings in the sequence-based computer file.

24. The method of clause 23, wherein comparing the plurality of target text strings to the ambiguous text strings in the sequence-based computer file comprises comparing each target text string to each ambiguous text string that is associated with the same locus as that target text string.

25. The method of clause 17 or clause 18, further comprising receiving a target computer file comprising a plurality of target text strings, wherein each target text string represents nucleotide sequence data generated by a read of a massively parallel sequencing (MPS) instrument, and comparing the plurality of target text strings to the ambiguous text strings in each of the plurality of sequence-based computer files to detect whether each of the target text strings matches at least one of the ambiguous text strings in any one of the plurality of sequence-based computer files.

26. The method of clause 25, wherein comparing the plurality of target text strings to the ambiguous text strings in each of the plurality of sequence-based computer files comprises, for each sequence-based computer file, comparing each target text string to each ambiguous text string in that sequence-based computer file that is associated with the same locus as that target text string.

27. One or more computer-readable media comprising a plurality of instructions that, when executed by one or more processors, causes the one or more processors to perform the method of any one of clauses 1-26.

28. A sequence-based computer file created according to the method of any one of clauses 1-15.

29. A database comprising a plurality of sequence-based computer files, wherein each of the plurality of sequence-based computer files was created according to the method of any one of clauses 1-15.

30. A computer file storing sequence-based short tandem repeat (STR) profiling data for a DNA sample, the computer file comprising a plurality of ambiguous text strings each representing an STR region of a locus of the DNA sample, wherein each ambiguous text string consists of a sequence of ambiguous characters extending from a start coordinate to a stop coordinate of the STR region represented by that ambiguous text string.

31. The computer file of clause 30, wherein each ambiguous character of each ambiguous text is a text character used to represent an ambiguous base call.

32. The computer file of clause 30 or clause 31, further comprising locus data associated with each ambiguous text string, wherein the locus data identifies the locus containing the STR region represented by the associated ambiguous text string.

33. The computer file any one of clauses 30-32, further comprising coordinate data associated with each ambiguous text string, wherein the coordinate data identifies the start and stop coordinates of the STR region represented by the associated ambiguous text string.

34. The computer file any one of clauses 30-33, wherein the computer file represents a DNA profile of a human.

35. A method comprising receiving a target text string that represents nucleotide sequence data generated by a read of a massively parallel sequencing (MPS) instrument and comparing the target text string to each ambiguous text string in a computer file according to any one of clauses 30-34 to detect any ambiguous text string in the computer file that matches the target text string.

36. A method comprising receiving a target computer file comprising a plurality of target text strings, wherein each target text string represents nucleotide sequence data generated by a read of a massively parallel sequencing (MPS) instrument, and comparing each of the plurality of target text strings to each ambiguous text string in a computer file according to any one of clauses 30-34 to detect any ambiguous text string in the computer file that matches any of the target text strings.

37. A method comprising receiving a target computer file comprising a plurality of target text strings, wherein each target text string represents nucleotide sequence data generated by a read of a massively parallel sequencing (MPS) instrument, and comparing the plurality of target text strings to the ambiguous text strings in a computer file according to any one of clauses 30-34 to detect whether each of the target text strings matches at least one of the ambiguous text strings in the computer file.

38. The method of clause 37, wherein comparing the plurality of target text strings to the ambiguous text strings in the computer file comprises comparing each target text string to each ambiguous text string that is associated with the same locus as that target text string.

39. A database comprising a plurality of computer files, wherein each of the plurality of computer files stores sequence-based short tandem repeat (STR) profiling data for a DNA sample in the form of a plurality of ambiguous text strings each representing an STR region of a locus of the DNA sample, wherein each ambiguous text string consists of a sequence of ambiguous characters extending from a start coordinate to a stop coordinate of the STR region represented by that ambiguous text string.

40. The database of clause 39, wherein each ambiguous character of each ambiguous text is a text character used to represent an ambiguous base call.

41. The database of clause 39 or clause 40, wherein each of the plurality of computer files further stores locus data associated with each ambiguous text string, wherein the locus data identifies the locus containing the STR region represented by the associated ambiguous text string.

42. The database of any one of clauses 39-41, wherein each of the plurality of computer files further stores coordinate data associated with each ambiguous text string, wherein the coordinate data identifies the start and stop coordinates of the STR region represented by the associated ambiguous text string.

43. The database any one of clauses 39-42, wherein each of the plurality of computer files represents a DNA profile of a human.

44. A method comprising receiving a target text string that represents nucleotide sequence data generated by a read of a massively parallel sequencing (MPS) instrument and comparing the target text string to each ambiguous text string in a plurality of computer files of a database according to any one of clauses 39-43 to detect any ambiguous text string in the plurality of computer files that matches the target text string.

45. A method comprising receiving a target computer file comprising a plurality of target text strings, wherein each target text string represents nucleotide sequence data generated by a read of a massively parallel sequencing (MPS) instrument, and comparing each of the plurality of target text strings to each ambiguous text string in a plurality of computer files of a database according to any one of clauses 39-43 to detect any ambiguous text string in the plurality of computer files that matches any of the target text strings.

46. A method comprising receiving a target computer file comprising a plurality of target text strings, wherein each target text string represents nucleotide sequence data generated by a read of a massively parallel sequencing (MPS) instrument, and comparing the plurality of target text strings to the ambiguous text strings in each of a plurality of computer files of a database according to any one of clauses 39-43 to detect whether each of the target text strings matches at least one of the ambiguous text strings in any one of the plurality of computer files of the database.

47. The method of clause 46, wherein comparing the plurality of target text strings to the ambiguous text strings in each of the plurality of computer files of the database comprises, for each computer file of the database, comparing each target text string to each ambiguous text string in that computer file that is associated with the same locus as that target text string.

BRIEF DESCRIPTION OF DRAWINGS

The concepts described in the present disclosure are illustrated by way of example and not by way of limitation in the accompanying figures. For simplicity and clarity of illustration, elements illustrated in the figures are not necessarily drawn to scale. Further, where considered appropriate, reference labels have been repeated among the figures to indicate corresponding or analogous elements. The Detailed Description of Illustrative Embodiments below particularly refers to the accompanying figures in which:

FIG. 5 is a simplified flow diagram illustrating one embodiment of a method of recoding one or more repeat-based designations of a first computer file into a corresponding one or more sequence-based ambiguous text strings, storing the one or more sequence-based ambiguous text strings in a second computer file, and detecting one or more sequence-based ambiguous text strings that match a target text string.

DETAILED DESCRIPTION OF ILLUSTRATIVE EMBODIMENTS

Figure 1:
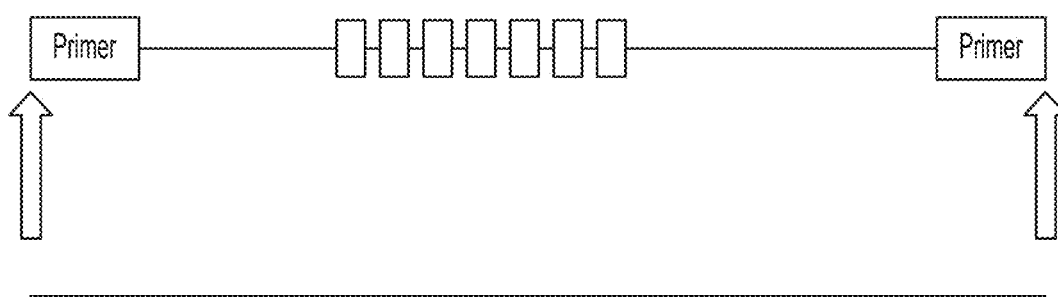
FIG. 1 is a simple diagram illustrating traditional STR typing by repeat number.

While the concepts of the present disclosure are susceptible to various modifications and alternative forms, specific embodiments thereof have been shown by way of example in the drawings and will be described herein in detail. It should be understood, however, that there is no intent to limit the concepts of the present disclosure to the particular forms disclosed, but on the contrary, the intention is to cover all modifications, equivalents, and alternatives consistent with the present disclosure and the appended claims.

References in the description to "one embodiment," "an embodiment," "an illustrative embodiment," etc., indicate that the embodiment described may include a particular feature, structure, or characteristic, but every embodiment may or may not necessarily include that particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to effect such feature, structure, or characteristic in connection with other embodiments whether or not explicitly described.

The disclosed embodiments may be implemented, in some cases, in hardware, firmware, software, or any combination thereof. The disclosed embodiments may also be implemented as instructions carried by or stored on a transitory or non-transitory computer-readable storage medium, which may be read and executed by one or more processors. A computer-readable storage medium may be embodied as any storage device, mechanism, or other physical structure for storing or transmitting information in a form readable by a computing device (e.g., a volatile or non-volatile memory, a media disc, or other media device). As used in the present disclosure, the term "computer file" refers to any data structure (including discrete data structures, as well as portions or subparts of discrete data structures) readable by a computer.

In the drawings, some structural or method features may be shown in specific arrangements and/or orderings. However, it should be appreciated that such specific arrangements and/or orderings may not be required. Rather, in some embodiments, such features may be arranged in a different manner and/or order than shown in the illustrative figures. Additionally, the inclusion of a structural or method feature in a particular figure is not meant to imply that such feature is required in all embodiments and, in some embodiments, may not be included or may be combined with other features.

The present disclosure relates to a common data format for storing, exchanging, and/or preserving DNA evidence in the form of nucleotide sequence data, including short tandem repeat (STR) profiling data. Specifically, the present disclosure relates to creating a new sequence-based computer file from an existing repeat-based computer file such that the new sequence-based computer file may then be used in methods and/or workflows that rely on DNA sequence (rather than number of repeats) for analysis and comparison purposes.

Commonly accepted and readily available reference sequences may be used to identify a genomic location (locus) of a particular DNA sequence. These reference sequences are designated first by the chromosome, and then by a coordinate system that defines which of the two arms of the chromosome the sequence is found, followed by a locus identifier and an actual base pair number that specifies the locus to the DNA sequence level. Hence, any genetic locus can be identified and defined by specifying a reference genome and two genome coordinates (i.e., start and stop coordinates) contained therein. The FBI and other law enforcement agencies around the world have selected about twenty-four specific STR loci for use in forensic DNA analysis applications. These STR loci have been selected because they are highly polymorphic, i.e., multiple alleles exist within the relevant populations. For example, the thirteen STR loci considered by the FBI as their "core" loci each exhibit at least eight different common allelic forms.

As discussed above, a sequence can be uniquely identified by specifying its start and stop coordinates with respect to a reference, along with the string of nucleotides contained in the DNA sequence itself. For standardization purposes, a reference may be employed so that a common nomenclature system that is based on a standard can be adopted. The start and stop coordinates of an amplified DNA fragment may be obtained by mapping the PCR amplification primers to a standard reference sequence. The DNA sequence of the amplified locus will contain the string of nucleotides (A, C, G. or T) between the start and stop coordinates. The length of the sequence (the number of nucleotides) may be obtained directly through the DNA typing procedure (whether repeat-based or sequence-based).

Fortunately, the human genome community has promulgated a number of such references, and continues to update them (generally called "builds") as more human genome information is obtained. One advantage of using these builds as reference standards is that a particular forensic locus can be defined down to the DNA sequence level, such that the sequence information obtained in a forensic case is available to the wider scientific community. Back-compatibility issues arise, however, when one attempts to compare a DNA sequence string to a repeat-based designation, and vice-versa. STRs typed as the number of repeats do not contain any sequence information, but simply a number of repeats inferred from the typing procedure.

The original association of a sequenced STR allele to the number of repeats observed in the sequence can be directly associated to a particular genome build, using a set of numbered coordinates arising therefrom. This is likely to arise from the genome build that was in place at the time the sequence was generated and then used to identify the potentially polymorphic STR locus. Hence, any changes in length that occur in later (or earlier) genome builds will be obtained by comparing two or more genomic coordinates to the coordinates that describe the region in the original reference. If the apparent lengths of alleles change in later (or any other) genome builds, this will be noted by simple genome build comparisons for length variation. Hence, other genome builds containing locus coordinates will always be comparable to the original, and all other, genome builds, provided the genome information is present in each genome build under comparison.

The original genome build coordinates sets the original length, confirmed by PCR amplicon size, to which other apparent lengths can then be compared. The apparent lengths in genome builds, however, are just alternative ways of describing the same thing, and are nothing more than a naming convention. Since the human genome is relatively stable as compared to reference coordinates, the actual size of the amplicons will not change as new genome builds are generated, but it may appear that the size is different if other genome builds with different coordinates are used. As long as one retains the identity of the genome build used to establish the sequence to repeat-number relationship, further conversions to other genome coordinate systems are straightforward.

Referring now to FIG. 1, DNA amplicons have traditionally been coded using repeat-based designations. In the case of FIG. 1, there are 7 repeats of the STR. As shown in FIG. 1, the lengths of the amplification primers, which do not originate from the donor, are typically incorporated into the amplicon during the amplification process and contribute to the overall size (length) of the product. Therefore, the amplicon consists of integrated primer sequences as a part of the allele length. The number of repeats is obtained by comparing the length to a reference that correlates a particular length to a particular number of repeats. It should be appreciated that, when converting the length of the amplicon to repeat length, the lengths of the primers are invariant. In a similar fashion to FIG. 1, a sequenced-based text string may be converted to a repeat-based designation by using the same simple conversion process.

Figure 2:
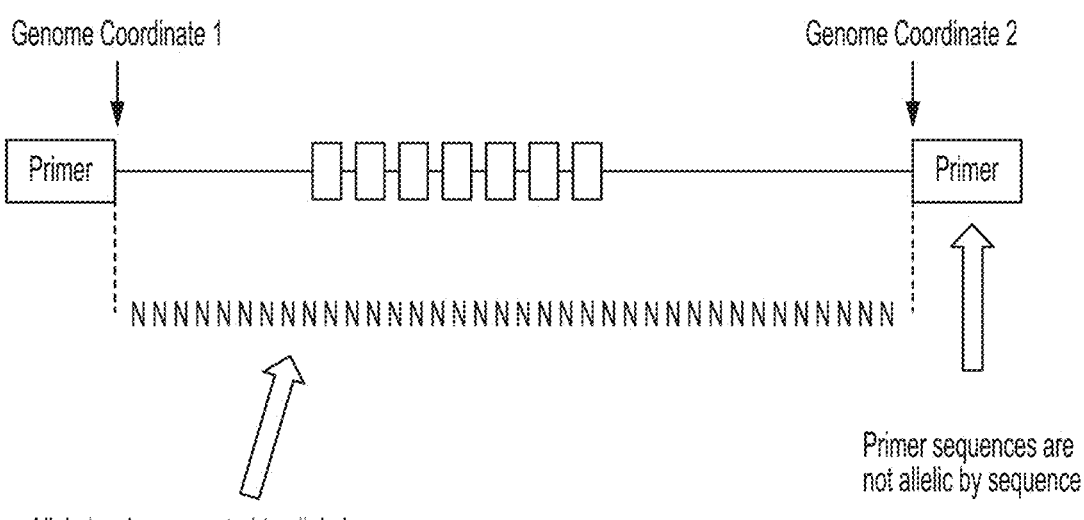
FIG. 2 is a simple diagram illustrating creation of a sequence-based ambiguous text string for the amplicon of FIG. 1 by excising the primer sequences and capturing the remaining length as a string of ambiguous sequence characters between two genome coordinate positions.
Figures 3, 4:
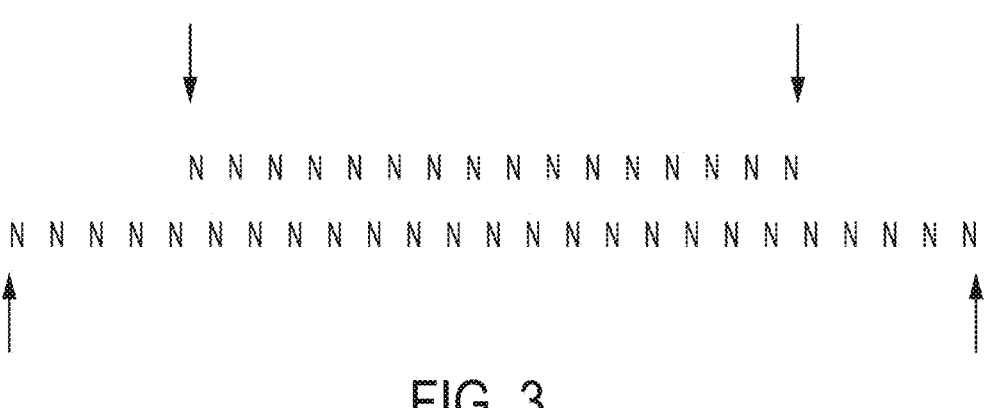
FIG. 3 is a simple diagram illustrating that sequence-based ambiguous text strings, derived from different repeat-based designations, can be differentiated by length.
FIG. 4 is a simple diagram illustrating that a sequence-based ambiguous text string (derived from a repeat-based designation) and a non-ambiguous sequence obtained by DNA sequencing that have the same genome coordinates are effectively the same by sequence (FIG. 4 discloses SEQ ID NO: 1)

Referring now to FIG. 2, sequence-based test strings can be employed as the unit of information for both repeat-based designations and sequence-based designations of DNA sequences. In order to accomplish this, ambiguous base calls can be used to describe lengths of amplicons that have not been sequenced. In addition to A, C, G, and T, genome sequence assemblies can include ambiguous characters reflecting ambiguous base calls (e.g., designated by "N"), which are used when the nucleotide at a particular position of a nucleic acid sequence is unknown. FIG. 2 shows a simple diagram to illustrate how a repeat-based designation may be recoded to a sequence-based text string, capturing the length between two primer sequences as a string of ambiguous sequence characters between two genome coordinate positions (i.e., start and stop coordinates). Since the resulting ambiguous text string is expressed as a number of ambiguous bases present between the start and stop coordinates, the resulting ambiguous text string has the same length as the corresponding repeat-based amplicon, as illustrated in FIG. 4. As a result, ambiguous text strings can be also differentiated from each other by length as illustrated in FIG. 3.

In contrast to the current repeat-based nomenclature system, which includes the amplification primers present in the product's size, the allelic sequence information should obtain exclusively from the donor. Current practices include the amplification primers as part of the allele length because they are incorporated into the amplicon during the amplification process and contribute to the overall size of the product. This does not pose an issue for the current method, as the primer lengths are invariant, and hence the conversion of amplicon length to a number of repeats is straightforward. However, with DNA sequencing technology, this is not the case, as the primer sequences do not arise from the DNA donor, and hence should be removed. Only genetic information from the donor is appropriate for sequence-based typing, and primer sequences may slightly differ from target sequences. FIG. 2 shows the relationship between amplicon lengths, genome coordinates, primer sequences, the allelic sequence, and a repeat-based designation converted to a sequence-based text string with the amplification primers excised (as only genetic information obtained from the donor is included in sequence-based typing).

Using a string of ambiguous characters as the sequence corresponding to a repeat-based designation is a powerful recoding step that allows cross-compatibility of different technologies. The start and stop coordinates are generally clearly defined and captured as part of the DNA type. These coordinates allow for the same genetic locus in each sample under comparison to be compared to others in a case or database. For example, in repeat-based loci, the alleles from a locus often differ in length, thereby resulting in a different number of ambiguous characters if expressed as a sequence (see FIG. 3). In that case, the start and stop coordinates ensure elimination of all other repeat-based variants in the search while retaining the repeat-based information in sequence form. By specifying a DNA sequence in this manner, it then becomes possible to compare the sequence to other DNA sequences from a case or a DNA database, using established rules of comparison.

Upon recoding of the repeat-based designation into a sequence-based text string, a common nomenclature system is thereby created that can use information from both repeat-based methods and sequencing technologies. The present disclosure allows for a common data format for storing, comparing, and searching DNA profiles for matches by sequence.

Referring now to FIG. 5, one illustrative method 100 is shown as a simplified flow diagram. The method 100 begins with step 102 where a processor 10 receives a first computer file that includes repeat-based STR profiling data. Since the STR profiling data stored in the first computer file is repeat-based, the sequence of each STR region is not known. Instead, each item of STR profiling data describes a repeat-based designation of an STR locus that has not been sequenced but has been sized using PCR from primers corresponding to a set of genome start and stop coordinates. For example, the STR profiling data may include a genomic locus of an STR region, defined by genomic coordinates of the genetic locus, a length of each STR amplification product, and an inferred number of repeats of the STR. As described above, because each repeat-based designation has been generated using PCR from corresponding amplification primers, the total length of the STR region equals the number of nucleotides between the start and stop coordinates of the STR region and the combined lengths of the amplification primers.

Once the first computer file is received, the processor 10 proceeds to step 104. At step 104, the processor 10 determines a locus associated with each item of repeat-based STR profiling data in the first computer file, including start and stop coordinates of each STR region. At step 106, a corresponding ambiguous text string is created for each STR region by using ambiguous base calls. Each of the resulting ambiguous text strings is designed to have a length that is the same as the total length of the corresponding STR locus represented by the repeat-based STR profiling data. Since the exact sequence of each STR locus is not known, it is not plausible to use the unambiguous nucleotide bases (A, C, G, and T) to create a corresponding text string. Instead, an ambiguous text string is created using genomic coordinates specifying the locus, consistent with the measured size of the amplified fragment. This conversion includes excising the length of the primer sequences, as well as other non-template based products, arising from the amplification process, and capturing the remaining length of the repeat-based amplicon as a string of ambiguous sequence characters between the start and stop coordinates of each STR locus. As described above, "N" is a commonly used ambiguous character (that may represent, for example, any of A, C, G, or T), but other ambiguous characters may also be used. Using ambiguous characters, a repeat-based designation is thereby recoded into a sequence-based text string.

Subsequently at step 108, a second computer file is generated. It should be appreciated that, in some embodiment, a second computer file may be generated at or prior to any step of method 100 prior to step 108. At step 108, the ambiguous text string resulting from step 106 is stored in the second computer file. The processor 10 is configured to repeat steps 102-108 until the repeat-based STR profiling data for each locus within the repeat-based STR profile is recoded into ambiguous text strings. Once all of the repeat-based STR profiling data is recoded into ambiguous text strings, the processor 10 proceeds to step 110. It should be appreciated that, in some embodiments, the processor may proceed to step 110 while running steps 102-108, simultaneously.

At step 110, the processor 10 receives a target text string generated by an MPS instrument. The target text string represents a nucleotide sequence of a target sample. At step 112, the processor 10 detects any ambiguous text strings from the second computer file that match the target text string. To do so, the processor 10 compares the unambiguous nucleotide sequence of the target text string and the ambiguous sequence of the ambiguous text strings. The ambiguous text string and the unambiguous target text string are effectively the same by sequence because the ambiguous character N designation is defined as any single nucleotide (see FIG. 4). Therefore, the unique characteristic of the ambiguous character allows the processor 10 to detect the ambiguous text strings in the second computer file that matches the non-ambiguous target text string by length. The matching of step 110 may be performed using any algorithm or function for detecting whether or not two text strings contain the same (or even similar) information. The present disclosure therefore provides the architecture for directly comparing repeat-based STR data of the first computer file to sequence-based STR data of the second computer file.

To avoid inadvertent adoption of an incorrect strand, the present disclosure allows both strands of the DNA sequence to be retained and searched as sequence-based text strings. Automated reverse complement mechanisms can be employed to ensure that strand confusion is obviated. Alternatively, metadata can be employed to include both of the two complementary strands for each string entry. In this way, should an incorrect complementary strand be inadvertently searched in a case, due to mistakes or nomenclature errors, the matching DNA sequence is assured of being identified.

While certain illustrative embodiments have been described in detail in the figures and the foregoing description, such an illustration and description is to be considered as exemplary and not restrictive in character, it being understood that only illustrative embodiments have been shown and described and that all changes and modifications that come within the spirit of the disclosure are desired to be protected. There exist a plurality of advantages of the present disclosure arising from the various features of the apparatus, systems, and methods described herein. It will be noted that alternative embodiments of the apparatus, systems, and methods of the present disclosure may not include all of the features described, yet still benefit from at least some of the advantages of such features. Those of ordinary skill in the art may readily devise their own implementations of the apparatus, systems, and methods that incorporate one or more of the features of the present disclosure.

---

---

The invention claimed is:

1. A method comprising:

operating a massively parallel sequencing (MPS) instrument to read nucleotide sequences present in a DNA sample to generate a first computer file comprising a plurality of target text strings representing the nucleotide sequences, wherein each target text string of the plurality of target text strings is associated with a locus of the DNA sample;

comparing the plurality of target text strings to a plurality of ambiguous text strings stored in a second computer file to detect whether each target text string aligns to a corresponding ambiguous text string of the plurality of ambiguous text strings that is associated with the same locus, wherein each ambiguous text string of the plurality of ambiguous text strings consists of a sequence of ambiguous characters used to represent ambiguous base calls by the MPS instrument; and identifying a human individual associated with the second computer file as a likely contributor to the DNA sample in response to detecting that a threshold number of the plurality of target text strings align to the plurality of ambiguous text strings of the second computer file.

2. The method of claim 1, wherein the sequence of ambiguous characters of each ambiguous text string extends from a start coordinate to a stop coordinate of a short tandem repeat (STR) region represented by that ambiguous text string.

3. The method of claim 2, wherein the second computer file further comprises (i) locus data associated with each ambiguous text string, wherein the locus data identifies the locus containing the STR region represented by the associated ambiguous text string, and (ii) coordinate data associated with each ambiguous text string, wherein the coordinate data identifies the start and stop coordinates of the STR region represented by the associated ambiguous text string.

4. The method of claim 1, wherein the second computer file was created from a legacy computer file that stored repeat-based and/or length-based short tandem repeat (STR) profiling data but no sequence data.

5. The method of claim 4, wherein the legacy computer file was obtained from the Combined DNA Index System (CODIS) database.

6. The method of claim 4, wherein the legacy computer file was obtained from the United Kingdom National DNA Database (NDNAD).

7. The method of claim 1, further comprising:

comparing the plurality of target text strings to another plurality of ambiguous text strings stored in a third computer file to detect whether each target text string aligns to a corresponding ambiguous text string of the another plurality of ambiguous text strings that is associated with the same locus, wherein each ambiguous text string of the another plurality of ambiguous text strings consists of a sequence of ambiguous characters used to represent ambiguous base calls by the MPS instrument; and determining whether the plurality of target text strings of the first computer file better aligns to the plurality of ambiguous text strings of the second computer file or to the another plurality of ambiguous text strings of the third computer file.

8. The method of claim 7, wherein the second computer file and the third computer file are each stored as a record in a database.

9. The method of claim 7, further comprising identifying a different human individual associated with the third computer file as a more likely contributor to the DNA sample than the human individual associated with the second computer file in response to determining that the plurality of target text strings of the first computer file better aligns to the another plurality of ambiguous text strings of the third computer file than to the plurality of ambiguous text strings of the second computer file.

10. The method of claim 7, wherein the sequence of ambiguous characters of each ambiguous text string extends from a start coordinate to a stop coordinate of a short tandem repeat (STR) region represented by that ambiguous text string.

11. The method of claim 10, wherein each of the second and third computer files further comprises (i) locus data associated with each ambiguous text string, wherein the locus data identifies the locus containing the STR region represented by the associated ambiguous text string, and (ii) coordinate data associated with each ambiguous text string, wherein the coordinate data identifies the start and stop coordinates of the STR region represented by the associated ambiguous text string.

12. The method of claim 7, wherein the second computer file was created from a legacy computer file that stored repeat-based and/or length-based short tandem repeat (STR)

profiling data but no sequence data, and wherein the third computer file was created from a different legacy computer file that stored repeat-based and/or length-based STR profiling data but no sequence data.

13. The method of claim 12, wherein the legacy computer file and the different legacy computer file were both obtained from the Combined DNA Index System (CODIS) database.

14. The method of claim 12, wherein the legacy computer file and the different legacy computer file were both obtained from the United Kingdom National DNA Database (NDNAD).

15. A non-transitory computer readable medium storing a plurality of instructions that are configured to cause a processor that executes the plurality of instructions to:

operate a massively parallel sequencing (MPS) instrument to read nucleotide sequences present in a DNA sample to generate a first computer file comprising a plurality of target text strings representing the nucleotide sequences, wherein each target text string of the plurality of target text strings is associated with a locus of the DNA sample;

compare the plurality of target text strings to a plurality of ambiguous text strings stored in a second computer file to detect whether each target text string aligns to a corresponding ambiguous text string of the plurality of ambiguous text strings that is associated with the same locus, wherein each ambiguous text string of the plurality of ambiguous text strings consists of a sequence of ambiguous characters used to represent ambiguous base calls by the MPS instrument; and identify a human individual associated with the second computer file as a likely contributor to the DNA sample in response to detecting that a threshold number of the plurality of target text strings align to the plurality of ambiguous text strings of the second computer file.

16. The non-transitory computer readable medium of claim 15, wherein the plurality of instructions are further configured to cause the processor to:

compare the plurality of target text strings to another plurality of ambiguous text strings stored in a third computer file to detect whether each target text string aligns to a corresponding ambiguous text string of the another plurality of ambiguous text strings that is associated with the same locus, wherein each ambiguous text string of the another plurality of ambiguous text strings consists of a sequence of ambiguous characters used to represent ambiguous base calls by the MPS instrument; and determine whether the plurality of target text strings of the first computer file better aligns to the plurality of ambiguous text strings of the second computer file or to the another plurality of ambiguous text strings of the third computer file.

* * * * *